United States Patent
Weir et al.

(10) Patent No.: US 11,712,300 B2
(45) Date of Patent: *Aug. 1, 2023

(54) SYSTEM AND METHOD FOR REDUCING BLADE EXPOSURES

(71) Applicant: INTUITIVE SURGICAL OPERATIONS, INC., Sunnyvale, CA (US)

(72) Inventors: David W. Weir, San Carlos, CA (US); Julie L. Berry, San Jose, CA (US); Melissa D. Lippiatt, Burlingame, CA (US); Daniel P. Saraliev, Soquel, CA (US); Melody Wu, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 382 days.

This patent is subject to a terminal disclaimer.

(21) Appl. No.: 16/930,239

(22) Filed: Jul. 15, 2020

(65) Prior Publication Data

US 2020/0337718 A1 Oct. 29, 2020

Related U.S. Application Data

(63) Continuation of application No. 15/573,031, filed as application No. PCT/US2016/032324 on May 13, 2016, now Pat. No. 10,743,897.

(51) Int. Cl.
*A61B 34/00* (2016.01)
*A61B 18/14* (2006.01)
(Continued)

(52) U.S. Cl.
CPC .......... *A61B 34/00* (2016.02); *A61B 17/285* (2013.01); *A61B 17/320016* (2013.01);
(Continued)

(58) Field of Classification Search
CPC .......... A61B 17/285; A61B 17/320016; A61B 18/1445; A61B 34/00; A61B 34/30;
(Continued)

(56) References Cited

U.S. PATENT DOCUMENTS 10,743,897 B2    8/2020   Weir et al.
2009/0125026 A1  5/2009   Rioux et al.
(Continued)

FOREIGN PATENT DOCUMENTS

CA    2664199 A1     10/2009
JP    2011092743 A   5/2011
(Continued)

OTHER PUBLICATIONS

Extended European Search Report for Application No. EP16797003.7 dated Dec. 13, 2018, 5 pages.
(Continued)

*Primary Examiner* — Sarah A Simpson
(74) *Attorney, Agent, or Firm* — Artegis Law Group, LLP

(57) ABSTRACT

Techniques for reducing blade exposures include one or more processors and a drive system configured to be coupled to a cutting instrument. The cutting instrument includes an end effector located at a distal end of the cutting instrument, the end effector comprising opposable gripping jaws and a cutting blade, a shaft configured to be coupled to the drive system, an articulated wrist coupling the end effector to the shaft and one or more drive mechanisms in the shaft for coupling force or torque from the drive system to the end effector and the articulated wrist. The one or more processors are configured to measure a jaw angle between the gripping jaws, measure articulation of the articulated wrist, correct the jaw angle based on the articulation of the
(Continued)

articulated wrist, determine a cutting length based on the corrected jaw angle, and perform a cutting operation according to the cutting length.

20 Claims, 8 Drawing Sheets

Related U.S. Application Data

(60) Provisional application No. 62/176,893, filed on May 15, 2015.

(51) Int. Cl.
*A61B 34/30* (2016.01)
*A61B 17/285* (2006.01)
*A61B 17/32* (2006.01)
*A61B 90/00* (2016.01)
*A61B 17/00* (2006.01)

(52) U.S. Cl.
CPC .......... *A61B 18/1445* (2013.01); *A61B 34/30* (2016.02); *A61B 2017/003* (2013.01); *A61B 2018/1455* (2013.01); *A61B 2034/305* (2016.02); *A61B 2090/067* (2016.02)

(58) Field of Classification Search
CPC ........ A61B 2017/003; A61B 2034/305; A61B 2018/1455; A61B 2090/067
See application file for complete search history.

(56) References Cited

U.S. PATENT DOCUMENTS

| | | |
|---|---|---|
| 2009/0287352 A1 | 11/2009 | Geist et al. |
| 2011/0009864 A1 | 1/2011 | Bucciaglia et al. |
| 2012/0209314 A1* | 8/2012 | Weir ..................... A61B 34/37 606/205 |
| 2012/0211546 A1 | 8/2012 | Shelton, IV |
| 2012/0215220 A1 | 8/2012 | Manzo |
| 2012/0310221 A1 | 12/2012 | Durant et al. |
| 2012/0310254 A1 | 12/2012 | Manzo et al. |
| 2013/0123783 A1 | 5/2013 | Marczyk |
| 2014/0052152 A1 | 2/2014 | Au et al. |
| 2014/0114327 A1 | 4/2014 | Boudreaux et al. |
| 2015/0051733 A1 | 2/2015 | Nowlin et al. |
| 2016/0089198 A1* | 3/2016 | Arya .................. A61B 18/1482 600/317 |
| 2016/0324588 A1 | 11/2016 | Durant et al. |
| 2018/0161052 A1 | 6/2018 | Weir et al. |
| 2019/0206564 A1 | 7/2019 | Shelton, IV et al. |

FOREIGN PATENT DOCUMENTS

| | | |
|---|---|---|
| JP | 2013131149 A | 7/2013 |
| JP | 2014176706 A | 9/2014 |
| KR | 20130108367 A | 10/2013 |
| WO | WO-2007111737 A2 | 10/2007 |
| WO | WO-2010109932 A1 | 9/2010 |
| WO | WO-2010117685 A2 | 10/2010 |
| WO | WO-2012112888 A2 | 8/2012 |

OTHER PUBLICATIONS

Extended European Search Report for Application No. EP20159149.2 dated Jun. 17, 2020, 7 pages.
International Search Report and Written Opinion for Application No. PCT/US2016/032324, dated Aug. 18, 2016, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

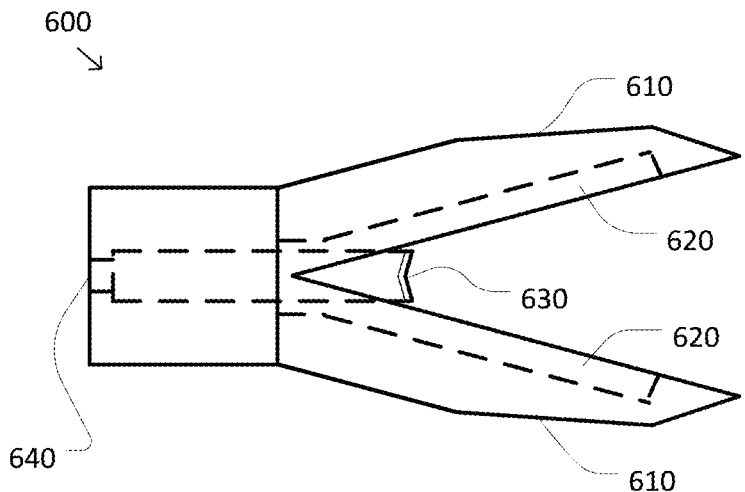
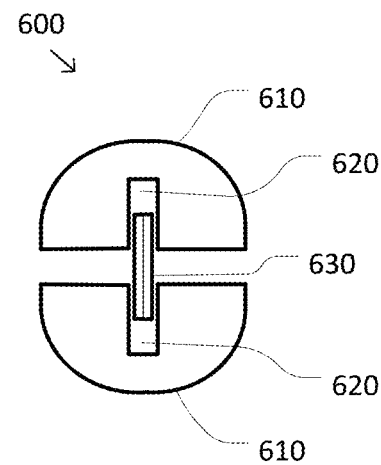
FIG. 6A
FIG. 6B
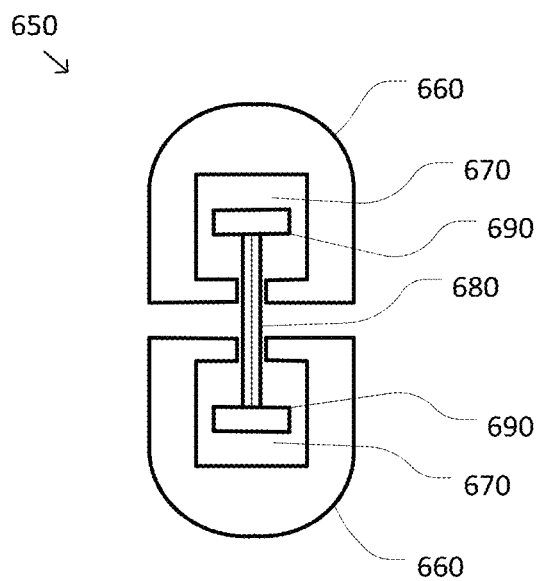
FIG. 6C

SYSTEM AND METHOD FOR REDUCING BLADE EXPOSURES

RELATED APPLICATIONS

This patent application is a continuation of U.S. patent application Ser. No. 15/573,031 filed on Nov. 9, 2017, which is a U.S. National Stage patent application of International Patent Application No. PCT/US2016/032324 filed on May 13, 2016, which claims priority benefit of U.S. Provisional Patent Application titled "SYSTEM AND METHOD FOR REDUCING BLADE EXPOSURES", filed May 15, 2015 and having Ser. No. 62/176,893. entitled each of which is incorporated by reference herein in its entirety. The subject matter of these related applications is hereby incorporated herein by reference.

TECHNICAL FIELD

The present disclosure relates generally to operation of devices with articulated arms and end effectors and more particularly to operation of a minimally invasive cutting instrument so as to reduce blade exposures.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

Minimally invasive surgical techniques using computer-assisted medical devices generally attempt to perform surgical and/or other procedures while minimizing damage to healthy tissue. Some minimally invasive procedures may be performed remotely through the use of computer-assisted medical devices with surgical instruments. With many computer-assisted medical devices, a surgeon and/or other medical personnel may typically manipulate input devices using one or more controls on an operator console. As the surgeon and/or other medical personnel operate the various controls at the operator console, the commands are relayed from the operator console to a patient side device to which one or more end effectors and/or surgical instruments are mounted. In this way, the surgeon and/or other medical personnel are able to perform one or more procedures on a patient using the end effectors and/or surgical instruments. Depending upon the desired procedure and/or the surgical instruments in use, the desired procedure may be performed partially or wholly under control of the surgeon and/or medical personnel using teleoperation and/or under semi-autonomous control where the surgical instrument may perform a sequence of operations based on one or more activation actions by the surgeon and/or other medical personnel.

Minimally invasive surgical instruments, whether actuated manually, teleoperatively, and/or semi-autonomously may be used in a variety of operations and/or procedures and may have various configurations. Many such instruments include an end effector mounted at a distal end of a shaft that may be mounted to the distal end of an articulated arm. In many operational scenarios, the shaft may be configured to be inserted (e.g., laparoscopically, thoracoscopically, and/or the like) through an opening (e.g., a body wall incision, a natural orifice, and/or the like) to reach a remote surgical site. In some instruments, an articulating wrist mechanism may be mounted to the distal end of the instrument's shaft to support the end effector with the articulating wrist providing the ability to alter an orientation of the end effector relative to a longitudinal axis of the shaft.

End effectors of different design and/or configuration may be used to perform different tasks, procedures, and functions so as to be allow the surgeon and/or other medical personnel to perform any of a variety of surgical procedures. Examples include, but are not limited to, cauterizing, ablating, suturing, cutting, stapling, fusing, sealing, etc., and/or combinations thereof. Accordingly, end effectors can include a variety of components and/or combinations of components to perform these surgical procedures.

Consistent with the goals of a minimally invasive procedure, the size of the end effector is typically kept as small as possible while still allowing it to perform its intended task. One approach to keeping the size of the end effector small is to accomplish actuation of the end effector through the use of one or more inputs at a proximal end of the surgical instrument, which is typically located externally to the patient. Various gears, levers, pulleys, cables, rods, bands, and/or the like, may then be used to transmit actions from the one or more inputs along the shaft of the surgical instrument and to actuate the end effector. In the case of a computer-assisted medical device with an appropriate surgical instrument, a transmission mechanism at the proximal end of the instrument interfaces with various motors, solenoids, servos, active actuators, hydraulics, pneumatics, and/or the like provided on an articulated arm of the patient side device or a patient side cart. The motors, solenoids, servos, active actuators, hydraulics, pneumatics, and/or the like typically receive control signals through a master controller and provide input in the form of force and/or torque at the proximal end of the transmission mechanism, which the various gears, levers, pulleys, cables, rods, bands, and/or the like ultimately transmit to actuate the end effector at the distal end of the transmission mechanism.

Because of the remote nature of the operation of such end effectors, it may be difficult in some cases for the surgeon and/or other medical personnel to know the position of one or more components of the end effector during actuation to perform a desired procedure. For example, in some cases, other portions of the surgical instrument, including the end effector itself, and/or parts of the anatomy of the patient may hide from view one or more components of the surgical instrument during the actuation of the one or more components. Additionally, when one or more of the components encounters a fault condition while attempting to perform the desired procedure, it may be difficult for the surgeon and/or other medical personnel to detect and/or correct the fault condition due to the limited visibility of the end effector, the limited space in which the surgical instrument operates, the limited access to the surgical instrument, the remote position of the end effector relative to the surgeon and/or other medical personnel, and/or the like.

In addition, safety conditions may also be a factor in the design and/or operation of the surgical instrument. In some examples, the end effector of a surgical tool, such as a cutting tool, may include a sharp cutting blade. When the cutting blade is not actively being used to cut, the cutting blade may be sheathed and/or garaged within a housing or garage on the end effector so that it is generally positioned where it cannot accidentally cut tissue of the patient and/or medical personnel manipulating the surgical tool during non-operation. Similarly, one or more delicate components of the end effector may also be sheathed and/or garaged to prevent damage to the delicate components during non-operation.

When the cutting blade is not able to be returned to the garage, an error called a blade exposure may occur. In some cases, a blade exposure may occur when tissue and/or other debris interfere with the path of the cutting blade toward the garage preventing retraction of the cutting blade into the garage after a cutting operation. In some cases, a blade exposure may occur when the cutting blade comes out of a groove or track in the end effector used to guide the cutting blade preventing retraction of the cutting blade into the garage. It is generally a good idea to avoid blade exposures as it is not always possible to correct the blade exposure and retract the cutting blade into the garage without first extracting the cutting tool and end effector from within the patient.

Accordingly, improved methods and systems for the operation of surgical instruments, such as a cutting instrument, are desirable. In some examples, it may be desirable to reduce the likelihood of a blade exposure.

SUMMARY

Consistent with some embodiments, a surgical cutting instrument for use with a computer-assisted medical device includes an end effector located at a distal end of the surgical cutting instrument, one or more drive units, a shaft coupled to the drive unit, an articulated wrist coupling the end effector to the shaft, and one or more drive mechanisms in the shaft for coupling force or torque from the one or more drive units to the end effector and the articulated wrist. The end effector includes opposable gripping jaws and a cutting blade. To perform a cutting operation, the surgical cutting instrument is configured to measure a jaw angle between the gripping jaws, measure articulation of the articulated wrist, correct the jaw angle based on the articulation of the articulated wrist, determine a restriction on the cutting operation based on the corrected jaw angle, and perform or prevent the cutting operation based on the restriction.

Consistent with some embodiments, a method of performing a cutting operation using a surgical cutting instrument for use with a computer-assisted medical device includes measuring by one or more processors and using one or more first sensors a jaw angle between gripping jaws of an end effector of the surgical cutting instrument, measuring by the one or more processors and using one or more second sensors articulation of an articulated wrist coupling the end effector to a shaft of the surgical cutting instrument, correcting by the one or more processors the jaw angle based on the articulation of the articulated wrist, determining by the one or more processors a restriction on the cutting operation based on the corrected jaw angle, and performing or preventing the cutting operation based on the restriction.

Consistent with some embodiments, a non-transitory machine-readable medium includes a plurality of machine-readable instructions which when executed by one or more processors associated with a computer-assisted medical device are adapted to cause the one or more processors to perform a method. The method includes measuring a jaw angle between gripping jaws of an end effector of a surgical cutting instrument operated by the computer-assisted medical device, measuring articulation of an articulated wrist coupling the end effector to a shaft of the surgical cutting instrument, correcting the jaw angle based on the articulation of the articulated wrist, determining a restriction on the cutting operation based on the corrected jaw angle, and performing or preventing the cutting operation based on the restriction using one or more drive units.

Consistent with some embodiments, a computer-assisted medical device includes one or more processors, an articulated arm, and a surgical instrument coupled to a distal end of the articulated arm. The surgical instrument includes an end effector located at a distal end of the surgical instrument. The end effector includes opposable gripping jaws and a cutting blade. The surgical instrument further includes one or more drive units located at a proximal end of the surgical instrument, a shaft coupled to the drive units, an articulated wrist coupling the shaft to the end effector, and one or more drive mechanisms in the shaft for coupling force or torque from the one or more drive units to the end effector and the articulated wrist. The computer-assisted medical device is configured to perform a cutting operation using the cutting blade by measuring a jaw angle between the gripping jaws, measuring articulation of the articulated wrist, correcting the jaw angle based on the articulation of the articulated wrist, determining a restriction on the cutting operation based on the corrected jaw angle, and performing or preventing the cutting operation based on the restriction.

BRIEF DESCRIPTION OF THE DRAWINGS

FIGS. 6A-6E are simplified diagrams of various side and front cut-away views of end effector and cutting blade configurations according to some embodiments.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1:
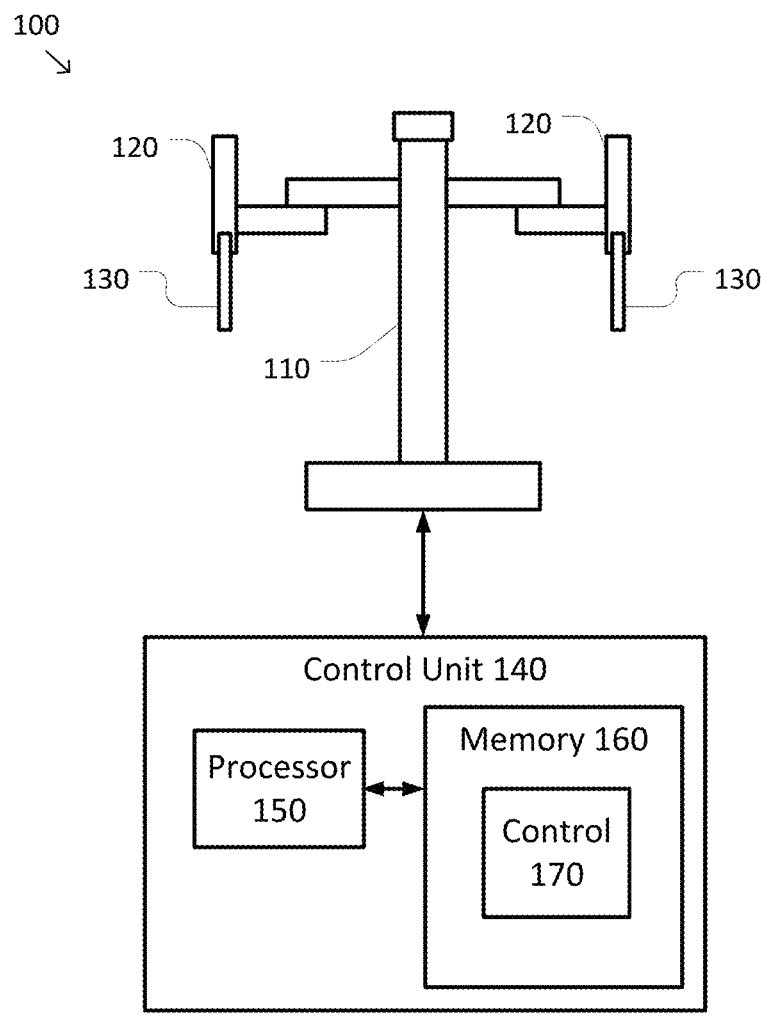
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a computer-assisted device 110 with one or more movable or articulated arms 120. Each of the one or more articulated arms 120 may support one or more instruments 130. In some examples, computer-assisted device 110 may be consistent with a computer-assisted surgical device. The one or more articulated arms 120 may each provide support for medical instruments 130 such as surgical instruments, imaging devices, and/or the like. In some examples, the instruments 130 may include end effectors that are capable of, but are not limited to, performing, gripping, retracting, cauterizing, ablating, suturing, cutting, stapling, fusing, sealing, etc., and/or combinations thereof.

Computer-assisted device 110 may further be coupled to an operator workstation (not shown), which may include one or more master controls for operating the computer-assisted device 110, the one or more articulated arms 120, and/or the instruments 130. In some examples, the one or more master controls may include master manipulators, levers, pedals, switches, keys, knobs, triggers, and/or the like. In some embodiments, computer-assisted device 110 and the operator workstation may correspond to a da Vinci® Surgical System commercialized by Intuitive Surgical, Inc. of Sunnyvale, Calif. In some embodiments, computer-assisted surgical devices with other configurations, fewer or more articulated arms, and/or the like may be used with computer-assisted system 100.

Computer-assisted device 110 is coupled to a control unit 140 via an interface. The interface may include one or more cables, fibers, connectors, and/or buses and may further include one or more networks with one or more network switching and/or routing devices. Control unit 140 includes a processor 150 coupled to memory 160. Operation of control unit 140 is controlled by processor 150. And although control unit 140 is shown with only one processor 150, it is understood that processor 150 may be representative of one or more central processing units, multi-core processors, microprocessors, microcontrollers, digital signal processors, field programmable gate arrays (FPGAs), application specific integrated circuits (ASICs), and/or the like in control unit 140. Control unit 140 may be implemented as a stand-alone subsystem and/or board added to a computing device or as a virtual machine. In some embodiments, control unit 140 may be included as part of the operator workstation and/or operated separately from, but in coordination with the operator workstation.

Memory 160 may be used to store software executed by control unit 140 and/or one or more data structures used during operation of control unit 140. Memory 160 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown in FIG. 1, memory 160 includes a control application 170 that may be used to support autonomous, semiautonomous, and/or teleoperated control of computer-assisted device 110. Control application 170 may include one or more application programming interfaces (APIs) for receiving position, motion, force, torque, and/or other sensor information from computer-assisted device 110, articulated arms 120, and/or instruments 130, exchanging position, motion, force, torque, and/or collision avoidance information with other control units regarding other devices, and/or planning and/or assisting in the planning of motion for computer-assisted device 110, articulated arms 120, and/or instruments 130. In some examples, control application 170 may further support autonomous, semiautonomous, and/or teleoperated control of the instruments 130 during a surgical procedure. And although control application 170 is depicted as a software application, control application 170 may be implemented using hardware, software, and/or a combination of hardware and software.

In some embodiments, computer-assisted system 100 may be found in an operating room and/or an interventional suite. And although computer-assisted system 100 includes only one computer-assisted device 110 with two articulated arms 120 and corresponding instruments 130, one of ordinary skill would understand that computer-assisted system 100 may include any number of computer-assisted devices with articulated arms and/or instruments of similar and/or different in design from computer-assisted device 110. In some examples, each of the computer-assisted devices may include fewer or more articulated arms and/or instruments.

Figure 2:
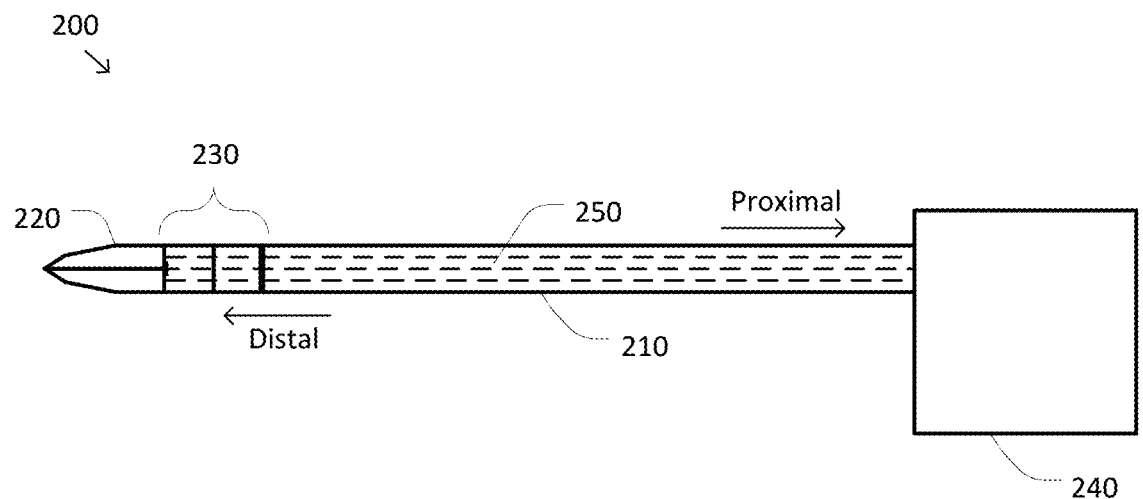
FIG. 2 is a simplified diagram showing a minimally invasive surgical instrument according to some embodiments.

FIG. 2 is a simplified diagram showing a minimally invasive surgical instrument 200 according to some embodiments. In some embodiments, surgical instrument 200 may be consistent with any of the instruments 130 of FIG. 1. The directions "proximal" and "distal" as depicted in FIG. 2 and as used herein help describe the relative orientation and location of components of surgical instrument 200. Distal generally refers to elements in a direction further along a kinematic chain from a base of a computer-assisted device, such as computer-assisted device 110, and/or or closest to the surgical work site in the intended operational use of the surgical instrument 200. Proximal generally refers to elements in a direction closer along a kinematic chain toward the base of the computer-assisted device and/or one of the articulated arms of the computer-assisted device.

As shown in FIG. 2, surgical instrument 200 includes a long shaft 210 used to couple an end effector 220 located at a distal end of shaft 210 to where the surgical instrument 200 is mounted to an articulated arm and/or a computer-assisted device at a proximal end of shaft 210. Depending upon the particular procedure for which the surgical instrument 200 is being used, shaft 210 may be inserted through an opening (e.g., a body wall incision, a natural orifice, and/or the like) in order to place end effector 220 in proximity to a remote surgical site located within the anatomy of a patient. As further shown in FIG. 2, end effector 220 is generally consistent with a two-jawed gripper-style end effector, which in some embodiments may further include a cutting and/or a fusing or sealing mechanism as is described in further detail below with respect to FIGS. 3 and 4A-4C. However, one of ordinary skill would understand that different surgical instruments 200 with different end effectors 220 are possible and may be consistent with the embodiments of surgical instrument 200 as described elsewhere herein.

A surgical instrument, such as surgical instrument 200 with end effector 220 typically relies on multiple degrees of freedom (DOFs) during its operation. Depending upon the configuration of surgical instrument 200 and the articulated arm and/or computer-assisted device to which it is mounted, various DOFs that may be used to position, orient, and/or operate end effector 220 are possible. In some examples, shaft 210 may be inserted in a distal direction and/or retreated in a proximal direction to provide an insertion DOF that may be used to control how deep within the anatomy of the patient that end effector 220 is placed. In some examples, shaft 210 may be able rotate about its longitudinal axis to provide a roll DOF that may be used to rotate end effector 220. In some examples, additional flexibility in the position and/or orientation of end effector 220 may be provided by an articulated wrist 230 that is used to couple end effector 220 to the distal end of shaft 210. In some examples, articulated wrist 230 may include one or more rotational joints, such as one or more roll, pitch or yaw joints that may provide one or more "roll," "pitch," and "yaw" DOF(s), respectively, that may be used to control an orientation of end effector 220 relative to the longitudinal axis of shaft 210. In some examples, the one or more rotational joints may include a pitch and a yaw joint; a roll, a pitch, and a yaw joint, a roll, a pitch, and a roll joint; and/or the like. In some examples, end effector 220 may further include a grip DOF used to control the opening and closing of the jaws of end effector 220 and/or an activation DOF used to control the extension, retraction, and/or operation of a cutting mechanism as is described in further detail below.

Surgical instrument 200 further includes a drive system 240 located at the proximal end of shaft 210. Drive system 240 includes one or more components for introducing forces and/or torques to surgical instrument 200 that may be used to manipulate the various DOFs supported by surgical instrument 200. In some examples, drive system 240 may include one or more motors, solenoids, servos, active actuators, hydraulics, pneumatics, and/or the like that are operated based on signals received from a control unit, such as control unit 140 of FIG. 1. In some examples, the signals may include one or more currents, voltages, pulse-width modulated wave forms, and/or the like. In some examples, drive system 240 may include one or more shafts, gears, pulleys, rods, bands, and/or the like which may be coupled to corresponding motors, solenoids, servos, active actuators, hydraulics, pneumatics, and/or the like that are part of the articulated arm, such as any of the articulated arms 120, to which surgical instrument 200 is mounted. In some examples, the one or more drive inputs, such as shafts, gears, pulleys, rods, bands, and/or the like, may be used to receive forces and/or torques from the motors, solenoids, servos, active actuators, hydraulics, pneumatics, and/or the like and apply those forces and/or torques to adjust the various DOFs of surgical instrument 200.

In some embodiments, the forces and/or torques generated by and/or received by drive system 240 may be transferred from drive system 240 and along shaft 210 to the various joints and/or elements of surgical instrument 200 located distal to drive system 240 using one or more drive mechanisms 250. In some examples, the one or more drive mechanisms 250 may include one or more gears, levers, pulleys, cables, rods, bands, and/or the like. In some examples, shaft 210 is hollow and the drive mechanisms 250 pass along the inside of shaft 210 from drive system 240 to the corresponding DOF in end effector 220 and/or articulated wrist 230. In some examples, each of the drive mechanisms 250 may be a cable disposed inside a hollow sheath or lumen in a Bowden cable like configuration. In some examples, the cable and/or the inside of the lumen may be coated with a low-friction coating such as polytetrafluoroethylene (PTFE) and/or the like. In some examples, as the proximal end of each of the cables is pulled and/or pushed inside drive system 240, such as by wrapping and/or unwrapping the cable about a capstan or shaft, the distal end of the cable moves accordingly and applies a suitable force and/or torque to adjust one of the DOFs of end effector 220, articulated wrist 230, and/or surgical instrument 200.

Figure 3:
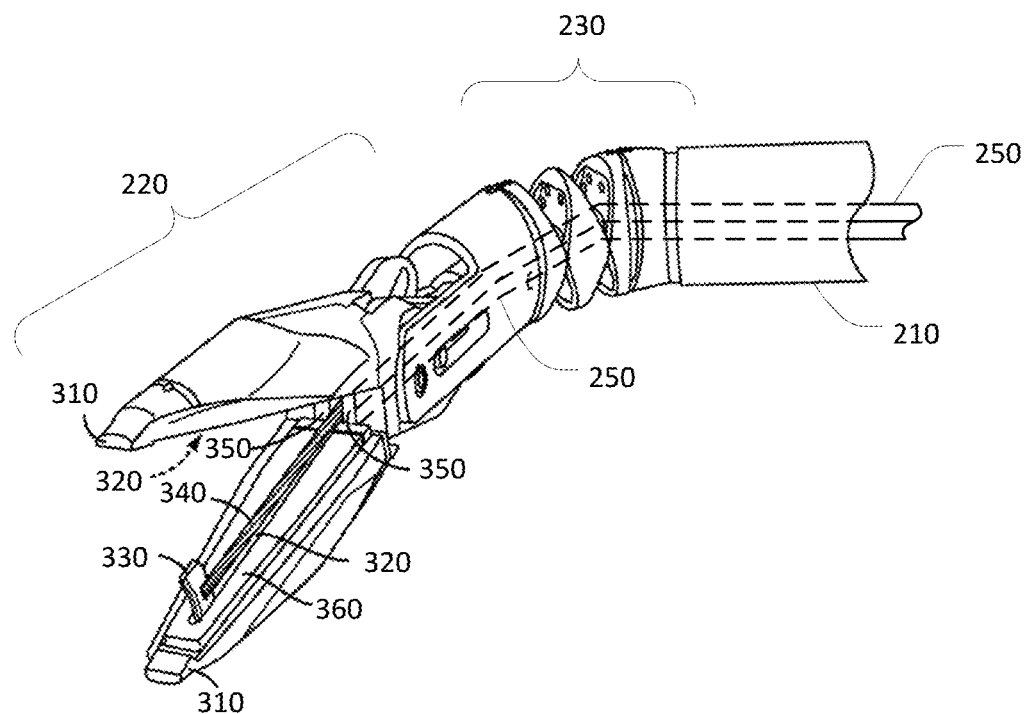
FIG. 3 is a simplified perspective diagram of the distal end of the surgical instrument of FIG. 2 according to some embodiments.

FIG. 3 is a simplified perspective diagram of the distal end of surgical instrument 200 according to some embodiments. As shown in FIG. 3, the distal end of surgical instrument 200 is depicted so as to show additional details of end effector 220, articulated wrist 230, and drive mechanisms 250. In more detail, end effector 220 includes opposing jaws 310 shown in an open position. Jaws 310 are configured to move between open and closed positions so that end effector 220 may be used during a procedure to grip and release tissue and/or other structures, such as sutures, located at the surgical site. In some examples, jaws 310 may be operated together as a single unit with both jaws 310 opening and/or closing at the same time. In some examples, jaws 310 may be opened and/or closed independently so that, for example, one jaw 310 could be held steady which the other jaw 310 may be opened and/or closed.

Figure 4A:
FIGS. 4A-4C are simplified cut-away diagrams of the end effector of FIGS. 2 and 3 according to some embodiments.
Figure 4B:
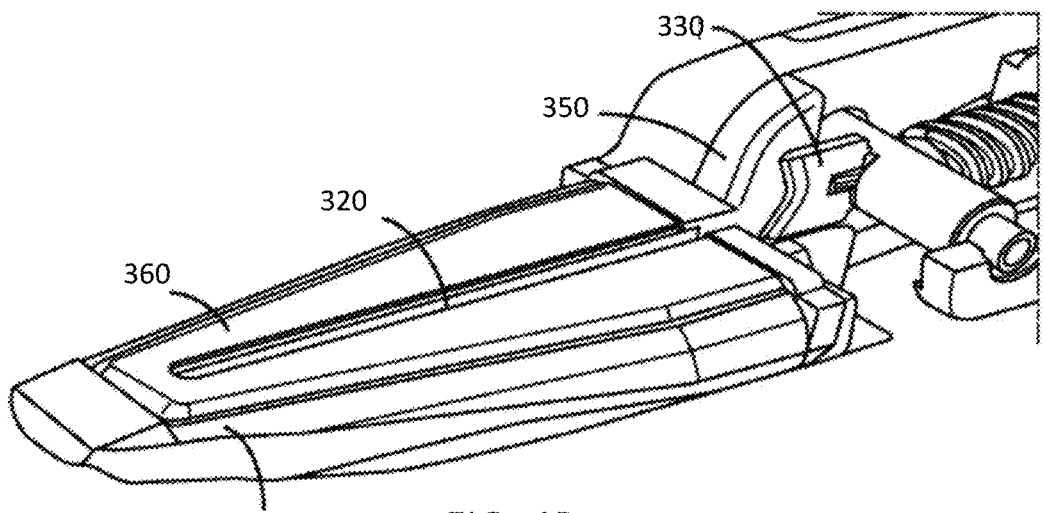
Figure 4C:
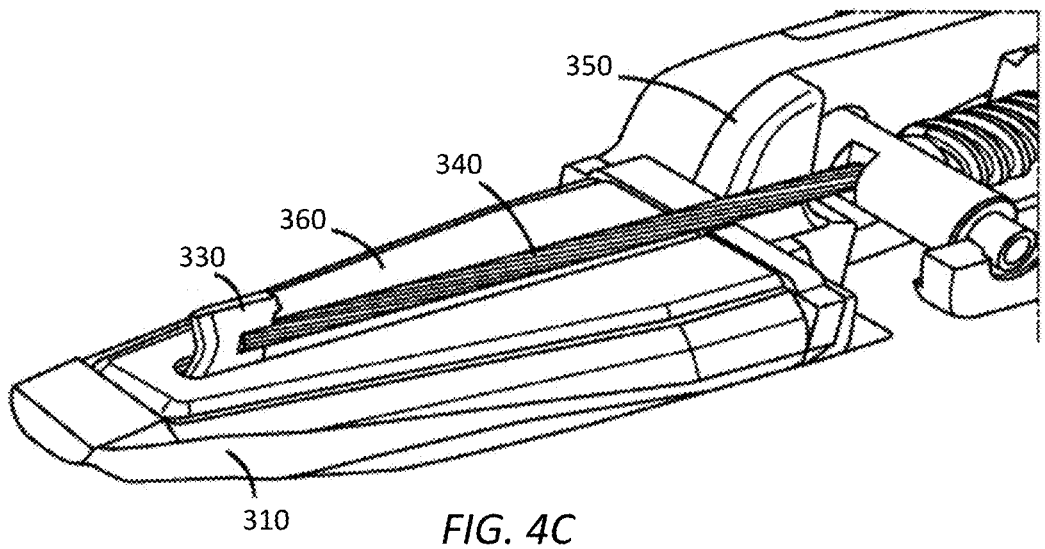

FIG. 3 shows that a gripping surface on an inside of each of jaws 310 includes a corresponding groove 320, which may act as a guide for a cutting blade 330, although the groove 320 may be omitted from one or more of jaws 310. As cutting blade 330 is extended toward the distal end of end effector 220 and/or retracted toward the proximal end of end effector 220, each of the grooves 320 may aid in the alignment and/or positioning of cutting blade 330 during a cutting operation. Extraction and/or retraction of cutting blade 330 is accomplished using a drive component 340 to which cutting blade 330 is attached. In some examples, drive component 340 pushes on cutting blade 330 to extend cutting blade 330 and pulls on cutting blade 330 to retract cutting blade 330. Use and positioning of cutting blade 330 is shown in FIGS. 4A-4C, which are simplified cut-away diagrams of end effector 220 according to some embodiments. FIG. 4A shows the relationship between cutting blade 330 and drive component 340.

End effector 220 further includes a garage feature 350 located at a proximal end of jaws 310. Garage feature 350 includes an opening through which both drive component 340 and cutting blade 330 may pass. Garage feature 350 is configured to provide a safe storage area for cutting blade 330 when cutting blade 330 is not in use. Thus, when cutting blade 330 is not actively being used as part of a cutting operation, end effector 220 is configured so that cutting blade 330 may be retracted into garage feature 350 in a "garaged" or stored position in which cutting blade 330 is recessed proximally behind jaws 310 as shown in FIG. 4B. Cutting blade 330 may additionally be extended to a position in which cutting blade 330 is positioned at or near a distal end of one of the grooves 320 as shown in FIG. 4C. In some examples, the positioning of cutting blade 330 as shown in FIG. 4C may correspond to a position of cutting blade 330 during a cutting operation.

In some examples, end effector 220 and surgical instrument 200 are designed so that the default or home position of cutting blade 330 is within garage feature 350. This arrangement of garage feature 350 may provide several features to end effector 220. In some examples, when cutting blade 330 is retracted into garage feature 350, the sharp cutting edge of cutting blade 330 is effectively sheathed so that cutting blade 330 is unlikely to accidentally cut tissue during a procedure and/or medical personnel handling surgical instrument 200 and/or end effector 220 before and/or after a procedure. In some examples, when cutting blade 330 is retracted into garage feature 350, cutting blade 330 may also be protected from damage, such as accidental dulling, when cutting blade 330 is not actively being used to cut.

Referring back to FIG. 3, in some embodiments, the gripping surface on the inside of each of jaws 310 may further include one or more optional electrodes 360. In some examples, electrodes 360 may be used to deliver electrosurgical energy to fuse tissue being held between jaws 310. In some examples, electrodes 360 may provide an electrocautery, fusing, and/or sealing feature to end effector 220 so that tissue may be cut and/or fused/sealed using the same surgical tool 200.

In some embodiments, operation of jaws 310, cutting blade 330, and/or the joints of articulated wrist 230 may be accomplished using corresponding ones of the drive mechanisms 250. In some examples, when jaws 310 are operated independently, a distal end of two of the drive mechanisms 250 (one for each of jaws 310) may be coupled to a respective jaw 310 so that as the corresponding drive mechanism 250 applies a pull and/or a pushing force (for example, using a cable, lead screw, and/or the like), the respective jaw 310 may be opened and/or closed. In some examples, when jaws 310 are operated together, both jaws 310 may be coupled to the distal end of the same drive mechanism 250. In some examples, drive component 340 may be coupled to a distal end of a corresponding drive mechanism 250 so that forces and/or torques applied to the corresponding drive mechanism 250 may be transferred to the push and/or pull motion of drive component 340. In some examples, additional drive mechanisms 350 may be used to operate the roll, pitch, and/or yaw DOFs in articulated wrist 230.

Figure 5:
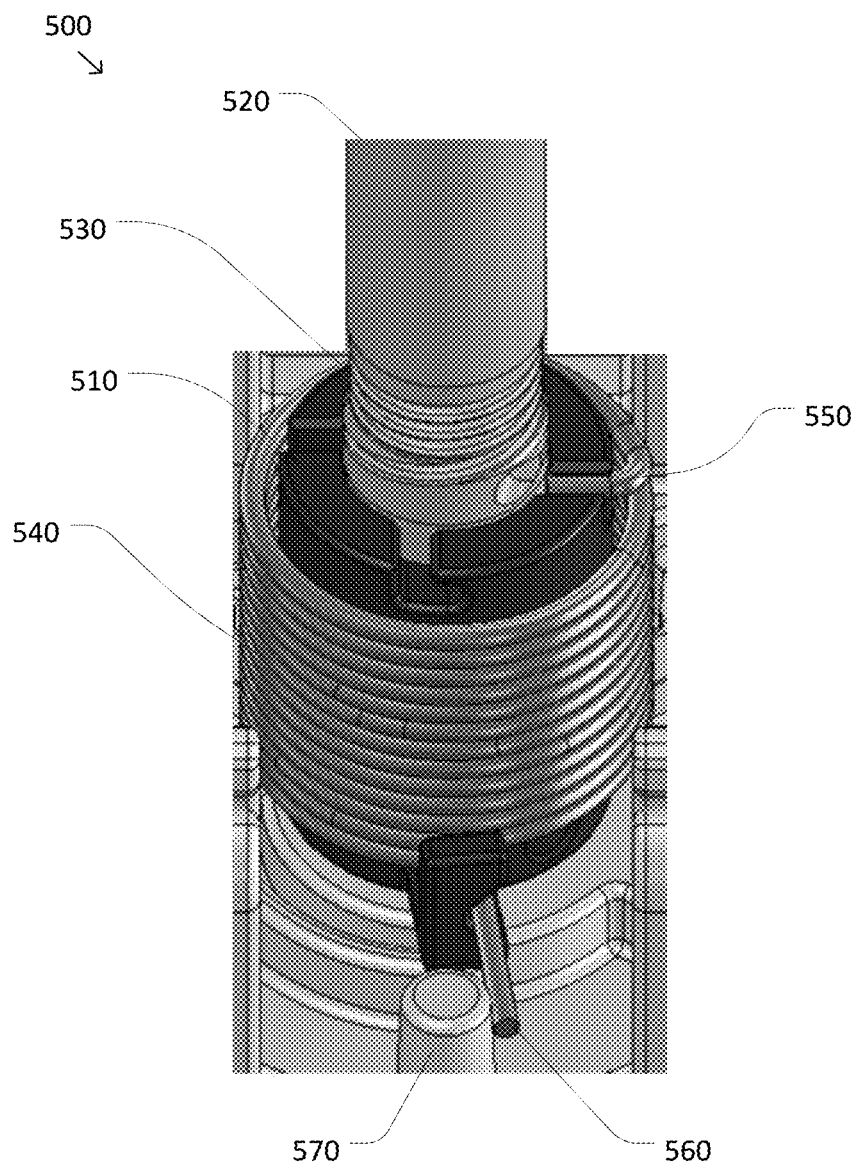
FIG. 5 is a simplified perspective diagram of a drive unit for a degree of freedom according to some embodiments.

FIG. 5 is a simplified perspective diagram of a drive unit 500 for a degree of freedom according to some embodiments. According to some embodiments, drive unit 500 may be representative of a portion of the components in drive system 240 of FIG. 2. As shown in FIG. 5, drive unit 500 is based on a rotational actuation approach in which a capstan 510 is rotated to actuate a DOF. Capstan 510 is coupled to a drive shaft 520 which may be the drive shaft of a motor, servo, active actuator, hydraulic actuator, pneumatic actuator, and/or the like (not shown). As torque is applied to drive shaft 520 and drive shaft 520 and capstan 510 are rotated, a cable 530 attached to capstan 510 and/or drive shaft 520 may be further wrapped around and/or unwrapped from around capstan 510 and/or drive shaft 520. When cable 530 is attached to the proximal end of a corresponding drive mechanism, such as any of drive mechanisms 250, the wrapping and unwrapping of the cable may translate into corresponding pulling and pushing forces and/or torques that may be applied to a DOF of an end effector located at the distal end of the drive mechanism. In some examples, rotation of capstan 510 and drive shaft 520 and the corresponding wrapping and/or unwrapping of cable 530 may result in opening and/or closing of gripper jaws such as jaws 310, extending and/or retracting of a cutting blade such as cutting blade 330, flexing and/or unflexing of articulated wrist joints, and/or the like. In some examples, monitoring a rotation angle and/or rotational velocity of capstan 510 and/or drive shaft 520 may also provide an indication of a current position and/or velocity of the corresponding DOF coupled to cable 530 through the corresponding drive mechanism. Thus, when drive unit 500 is used in conjunction with the DOFs of surgical instrument 200, the rotation angle and/or rotational velocity of capstan 510 and/or drive shaft 520 may provide useful feedback on the angle to which jaws 310 are opened, the position of cutting blade 330, and/or the pitch and/or yaw angle of articulated wrist 230 depending on which of the drive mechanisms 250 cable 530 is coupled.

Because it is often desirable for a DOF in an end effector to be configured with a default, rest, and/or home position when the DOF is not being actuated, in some embodiments a drive unit, such as drive unit 500 may include some type of resistive and/or restraining mechanism to return drive unit 500 to a corresponding home position. In some examples, use of a home position for a DOF may support configuration of a surgical instrument, such as surgical instrument 200, where gripping jaws are automatically closed and/or mostly closed, cutting blades are retracted into a garage feature, articulated wrist joints are straightened, and/or the like. As shown in FIG. 5, drive unit 500 includes a restraining mechanism in the form of a torsion spring 540. Torsion spring 540 is shown attached at one end 550 to capstan 510 and wrapped around capstan 510. As capstan 510 is rotated, a second end 560 of torsion spring 540 may freely rotate until it rotates up against a stop 570 that may be part of a body of drive unit 500. As capstan 510 continues to rotate after the second end 560 of torsion spring 540 is against stop 570, torsion spring 540 will begin to provide a restraining and/or return to home force and/or torque to capstan 510 as dictated by the amount of rotation of capstan 510 and a spring constant of torsion spring 540. Thus, as greater amounts of rotation are applied to capstan 510, torsion spring 540 applies increasing return to home force and/or torque to capstan 510. It is this return to home force and/or torque on capstan 510 that may be used, for example, to close the gripping jaws, retract the cutting blade, and/or straighten the articulated wrist joints.

Although FIG. 5 shows the restraining mechanism as a torsion spring wrapped around capstan 510, one of ordinary skill would recognize other possible restraining mechanisms and/or configurations for the restraining mechanisms to accomplish a similar restraining/return to home function. In some examples, the body of drive unit 500 may further include a second stop to provide a return to home force and/or torque to capstan 510 in an opposite direction to the return to home force and/or torque resulting from stop 570. In some examples, the second end 560 of torsion spring 540 may be mounted to the body of drive unit 500 so that no free movement of torsion spring 540 is permitted before torsion spring 540 begins applying return to home force and/or torque to capstan 510 and/or torsion spring 540 applies at least some return to home force and/or torque to capstan 510 even without rotation of capstan 510.

According to some embodiments, a cutting operation using a cutting tool, such as surgical instrument 200 with cutting blade 330 of FIGS. 3 and 4A-4C, typically involves a multi-phase operation. For example, a cutting operation may be accomplished by teleoperating an articulated arm to place end effector 220 in proximity to the tissue of interest. Articulated wrist 230 and jaws 310 may then be used to grasp the tissue of interest. Once the tissue of interest is held, a drive unit, such as drive unit 500, may be used to initiate a cutting action involving rapid extension of cutting blade 330 in a distal direction, holding cutting blade 330 at the extended position, and then retracting cutting blade 330 in a proximal direction until cutting blade 330 is returned to within garage feature 350. During the extension and retraction, cutting blade 330 may be guided by grooves 320 in jaws 310 so that the resulting cut occurs in a substantially straight line along the length of jaws 310.

In some cases, the cutting operation may not proceed as planned. In some examples, a blade exposure may occur where cutting blade 330 is not able to return to the home position within garage feature 350. In some examples, a blade exposure may occur when tissue and/or other debris interfere with the path of cutting blade 330 toward garage feature preventing retraction of cutting blade 330 into garage feature 350 during the retraction phase of the cutting operation. In some examples, a blade exposure may occur when cutting blade 330 twists and/or comes out of grooves 320. This may occur due to twisting force or torsion on cutting blade 330 caused by tissue, other debris, torsion forces from drive component 340 and/or drive mechanism 250, and/or the like. In some examples, preventing and/or reducing blade exposures is generally a good idea as it is not always possible to correct the blade exposure and retract the cutting blade into the garage without first extracting surgical instrument 200 and end effector 220 from within the patient.

Careful design and/or operation of the end effector and/or the cutting blade may be used to reduce the likelihood of blade exposures. FIGS. 6A-6E are simplified diagrams of various side and front cut-away views of end effector and cutting blade configurations according to some embodiments. FIGS. 6A and 6B are a simplified side and front cut-away view of an end effector 600 with a band-style cutting blade 630 that may be used to reduce blade exposures according to some embodiments. As shown in FIGS. 6A and 6B, end effector 600 includes jaws 610 that may be opened and closed to grasp tissue and other structures. FIGS. 6A and 6B show that a gripping face of each of jaws 610 may include a groove or slot 620 that may be used to guide band-style cutting blade 630 during the extension and retraction of band-style cutting blade 630, however groove 620 may be omitted from one or more of the gripping faces. The forces and/or torques used to extend and retract band-style cutting blade 630 are transmitted to band-style cutting blade 630 via drive component 640, which is generally similar to drive component 340.

As the front cut-away view of FIG. 6B shows, band-style cutting blade 630 may slide along the length of grooves 620 and may also slide up and down within grooves 620. Band-style cutting blade 630 includes a long blade that extends well into the proximal ends of end effector 600. The length of the long blade is selected so that, during the extension and retraction of the cutting operation, at least a portion of band-style cutting blade is designed to remain within grooves 620 at the proximal end of grooves 620 and jaws 610.

According to some embodiments, band-style cutting blade 630 of end effector 600 may be subject to several drawbacks that limit its effectiveness as a cutting tool. In some examples, the length of the long blade may interfere with the operation of jaws 610. In some examples, the length of the long blade may also preclude the use of an articulated wrist, such as articulated wrist 230, as the long blade may prevent flexing of the articulated wrist until the articulated wrist is located a longer than desirable distance from jaws 610. In some examples, when a blade exposure does occur using band-style cutting blade 630, the large size and long length of band-style cutting blade 630 may significantly interfere with the ability to close jaws 610 and/or clear the blade exposure without first removing end effector 600 from within the patient.

FIG. 6C is a simplified front cut-away view of an end effector 650 using an I-beam style cutting blade 680 according to some embodiments. As shown in FIG. 6C, jaws 660 each include a large slot 670 that include both an opening to a gripping surface of a respective jaw 660, but also include a widened slot area within the respective jaw 660. The upper and lower ends of I-beam style cutting blade 680 each include a widened end cap 690 that is larger in size than the opening to the gripping surface. These widened end caps 690 prevent the upper and lower ends of I-beam style cutting blade 680 from coming out of slots 670. Alternatively, when only one of jaws 660 includes large slot 670, a T-beam style cutting blade may be used instead of an I-beam style cutting blade.

According to some embodiments, I-beam style cutting blade 680 of end effector 650 may be subject to several drawbacks that limit its effectiveness as a cutting tool. In some examples, a height of slot 670 may unreasonably increase the cross section of end effector 650 so that it is not as useful as part of a minimally-invasive surgical instrument. In some examples, I-beam style cutting blade 680 may not be usable as part of a combined cutting and fusing or sealing end effector as it may not be possible to retract I-beam style cutting blade 680 completely from slots 670 as it may be difficult to reinsert end caps 690 into slots 670 after doing so. In some examples, when a blade exposure does occur using I-beam style cutting blade 680, such as due to tissue and/or other debris, end caps 690 act so as to lock jaws 660 in a closed and/or partially closed position. In some examples, when jaws 660 become locked while they are still gripping tissue, it may not be possible to remove end effector 650 from the patient without doing so surgically.

FIGS. 6D and 6E are simplified side and front cut-away views of end effector 220 from FIGS. 2, 3, and 4A-4C according to some embodiments. As described previously with respect to FIGS. 3 and 4A-4C, end effector 220 includes jaws 310 that may be opened and closed to grasp tissue and other structures. A gripping face of each of jaws 310 includes a groove or slot 320 that may be used to guide cutting blade 330 during the extension and retraction of cutting blade 330. The forces and/or torques used to extend and retract cutting blade 330 are transmitted to cutting blade 330 via drive component 340.

As the front cut-away view of FIG. 6E shows cutting blade 330 may slide along the length of grooves 320 and may also slide up and down within grooves 320. As shown, cutting blade 330 includes a much shorter blade than band-style cutting blade 630 so that end effector 220 may maintain a small cross-section and may also be used with articulated wrist 230. And even though the shorter blade of cutting blade 330 may increase the likelihood of a blade exposure relative to band-style blade 630 or I-beam style blade 680, the shorter blade may also improve the likelihood that a blade exposure may be cleared without removing end effector 220 from within the patient. In some examples, this is possible because the shorter blade may be easier to retract within garage feature 350 even though cutting blade 330 is not aligned with grooves 320.

Figure 7A:
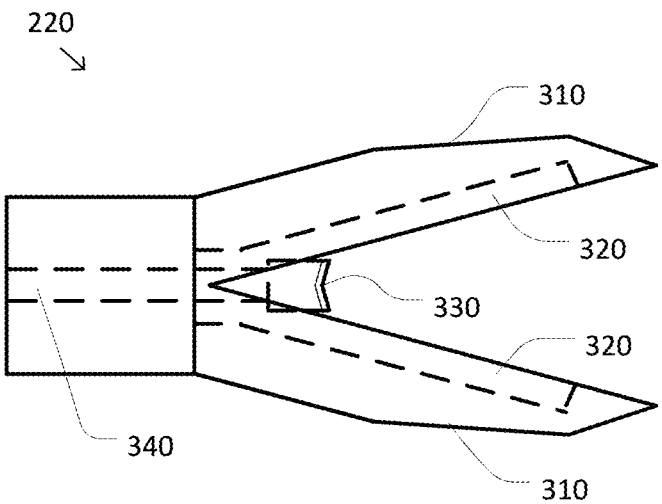
FIGS. 7A and 7B are simplified diagrams of models of a probability of blade exposure according to some embodiments.
Figure 7A:
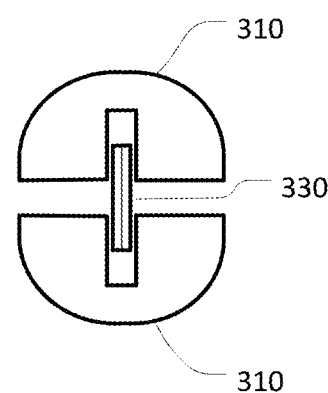
Figure 7A:
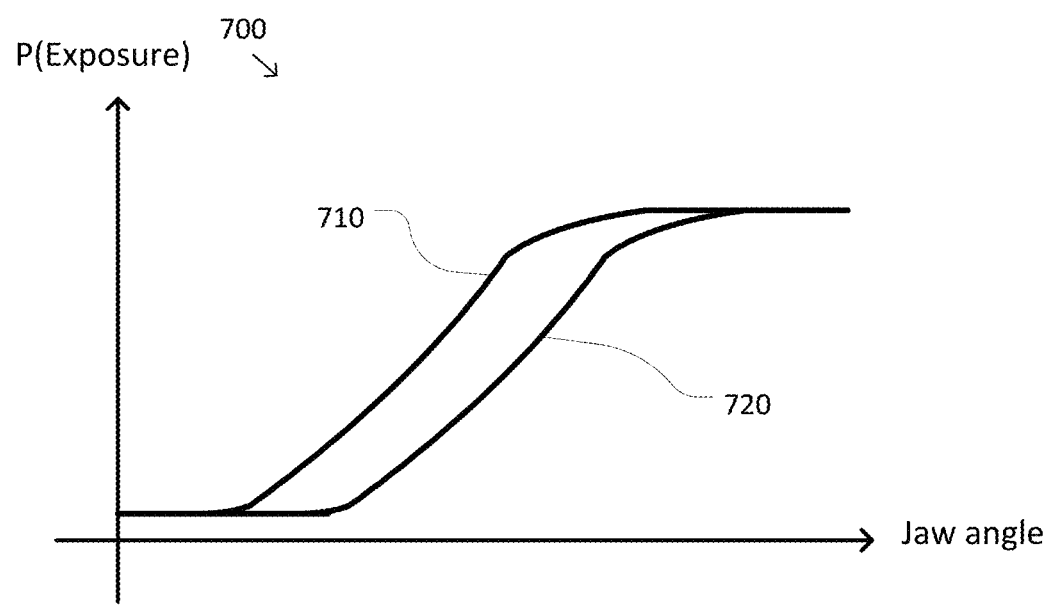
Figure 7B:
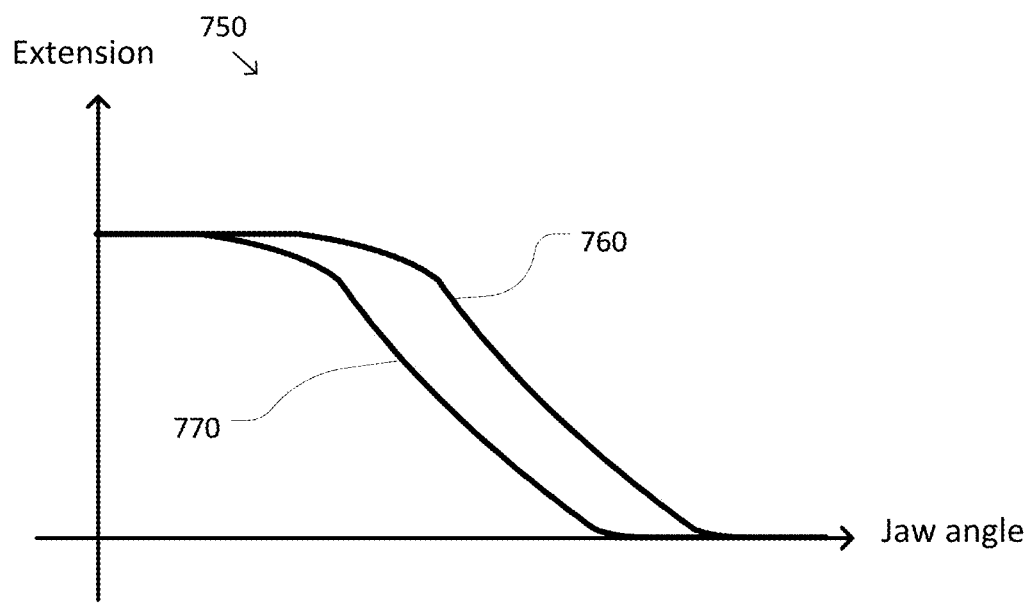

According to some embodiments, the likelihood of blade exposures may be reduced when using cutting blade 330 through proper operation of cutting blade 330 and end effector 220. In some examples, blade exposures may be reduced by preventing and/or restricting operation of cutting blade 330 based on a jaw angle of jaws 310. FIGS. 7A and 7B are simplified diagrams of models of a probability of blade exposure according to some embodiments. FIG. 7A depicts an example model 700 of a probability of blade exposure versus jaw angle for two possible lengths of cutting blade extension. Curves 710 and 720 both show a relatively low probability of blade exposure for narrow jaw angles, a region where the probability of a blade exposure increases rapidly with wider jaw angle, and a saturation region where the probability of blade exposure hits a maximum probability. Curve 710 corresponds to a case where the cutting blade is extended a longer distance than curve 720.

FIG. 7B depicts an example model 750 of cutting blade extension length versus jaw angle for two possible probabilities of blade exposure. Curves 760 and 770 both show a region where a full length cutting blade extension is possible at low jaw angles, a region where the length of cutting blade extension has to diminish rapidly as jaw angle increases to maintain a constant probability of blade exposure, and a region where little or no cutting blade extension is possible due to the wideness of the jaw angle without an unacceptable probability of blade exposure occurring. Curve 760 corresponds to a case where a higher tolerance (i.e., a higher probability) of blade exposure is permitted relative to curve 770.

Anecdotal evidence suggests that surgeons are willing to tolerate a certain likelihood that a blade exposure may occur in order to be able to cut thicker tissue that is held within the gripping jaws of the cutting tool. Consistent with this observation and according to some embodiments, the models and curves of FIGS. 7A and/or 7B may be used in one of two ways to manage the likelihood of blade exposure during a cutting operation.

In some examples, model 700 of FIG. 7A may be used to determine a maximum jaw angle for which cutting lengths of a predetermined distance are permitted. During operation of the cutting tool, cuts of the predetermined distance may be prohibited when the jaw angle exceeds the maximum jaw angle. In some examples, when the cutting length is 18 mm, the cutting blade 330 is 2.54 mm tall, and the tolerance for blade exposures is 10%, the maximum jaw angle may be approximately 7 degrees.

In some examples, model 750 of FIG. 7B may be used to limit a maximum cutting length based on the current jaw angle. During operation of the cutting tool, the jaw angle may be measured and, based on a tolerance for blade exposures, the measured jaw angle may be limited to the maximum cutting length.

Whether model 700 is used to prevent a cutting operation or model 750 is used to limit the cutting length of the cutting operation, the control application, such as control application 170 supervising and/or implementing the cutting operation uses a measurement of the current jaw angle to make the cut/no-cut decision and/or the cutting length determination. According to some embodiments, measurement of the jaw angle may not always be as accurate as desired to support these cutting determinations. As described previously with respect to FIG. 5, the jaw angle of the end effector, such as end effector 220, may, like the other DOFs of the end effector, be measured indirectly. In the examples, of FIG. 5, the jaw angle may be measured based on a rotation angle of the corresponding capstan 510 and/or drive shaft 520 from the one (joint jaw control) or two (independent jaw control) corresponding drive units 500 for the gripper jaws of the end effector. In some examples, as the articulated wrist flexes, the drive mechanism(s) used to operator the gripper jaws may be subject to bending and/or movement within the hollow shaft (e.g., shaft 210) of the surgical instrument. As the drive mechanism(s) bend and/or move an effective distance, as seen by the drive mechanism, may change between the distal end at the cutting blade and the proximal end at the drive unit. Thus, to obtain sufficient accuracy in the determination of the jaw angle, the jaw angle may have to be corrected based on the flex angle(s) of the articulated wrist and/or roll of the input shaft.

Figure 8:
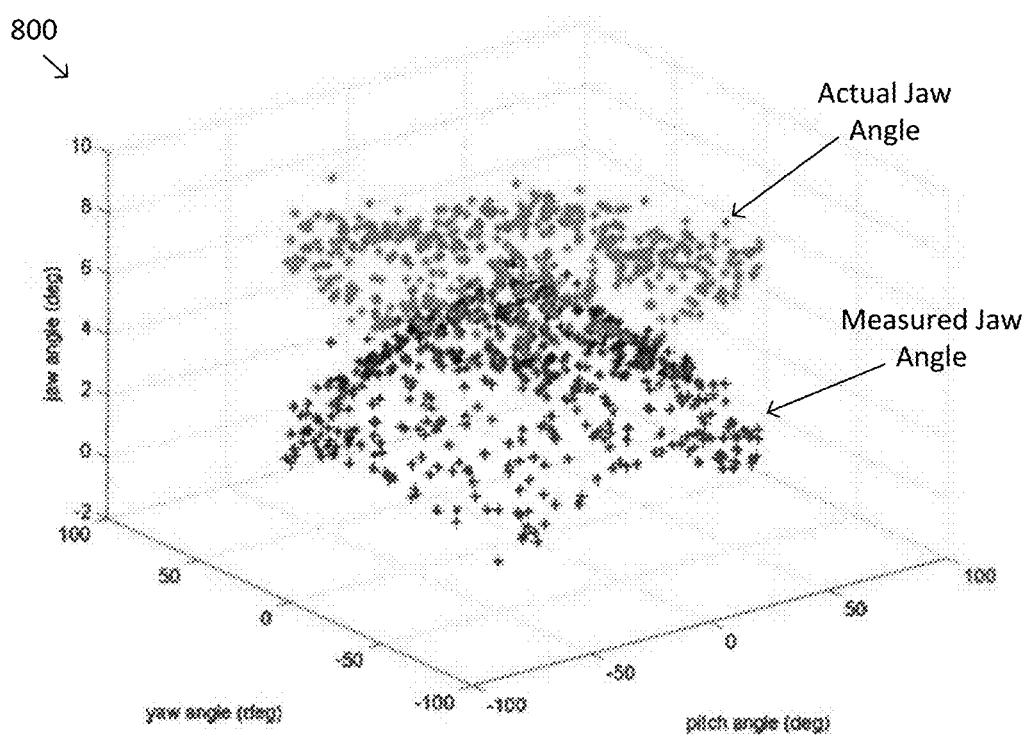
FIG. 8 is a simplified diagram of an exemplary relationship between actual and measured jaw angle according to some embodiments.

FIG. 8 is a simplified diagram of an exemplary relationship between actual and measured jaw angle according to some embodiments. FIG. 8 includes a scatter plot 800 from data collected using a surgical instrument consistent with surgical instrument 200. An end effector consistent with end effector 220 was used to grasp materials while an articulated wrist consistent with articulated wrist 230 was flexed to various combinations of pitch and yaw angles. At each of the combinations of pitch and yaw angles, an actual jaw angle between the gripping jaws was measured as represented by the lighter upper points in scatter plot 800. At each of the combinations of pitch and yaw angles, the jaw angle as measured at the drive unit for the gripping jaws was recorded as represented by the darker lower points in scatter plot 800. As shown in scatter plot 800, as both the pitch and yaw angles of the articulated wrist deviate from an angle of zero (corresponding to no flex in the articulated wrist and alignment of the end effector with the shaft of the surgical instrument) a greater divergence between actual and measured jaw angle occurred.

The data of scatter plot 800 was then matched to various models to determine a suitable model for the relationship and/or or function between actual jaw angle and measured jaw angle as pitch and yaw angle are varied. Experimentation indicated that a linear correction model consistent with Eq. 1 could be used to model the relationship between actual and measured jaw angle with a coefficient of determination or $R^2$ value in excess of 0.95.

$$\text{Actual jaw angle} = \text{measured jaw angle} + C_0 + C_1^*|\text{roll}| + C_2^*|\text{pitch}| + C_3^*|\text{yaw}| \quad \text{Eq. 1}$$

In some examples, the $C_0$, $C_1$, $C_2$, and $C_3$ coefficients may be modeled over a collection of surgical instruments or individually for each surgical instrument, with the coefficient values being recorded so that they are able to be accessed at run time based on an identifier, such as a serial number, of the corresponding surgical instrument. For one example of a surgical instrument consistent with surgical instrument 200, $C_0$ was found to be 0.000, $C_1$ was found to be 0.000, $C_2$ was found to be 0.062, and $C_3$ was found to be 0.069. The differences between $C_2$ and $C_3$ are due to differences in the design of the pitch and yaw joints as well as the location of the yaw joint more distal to the pitch joint.

Figure 9:
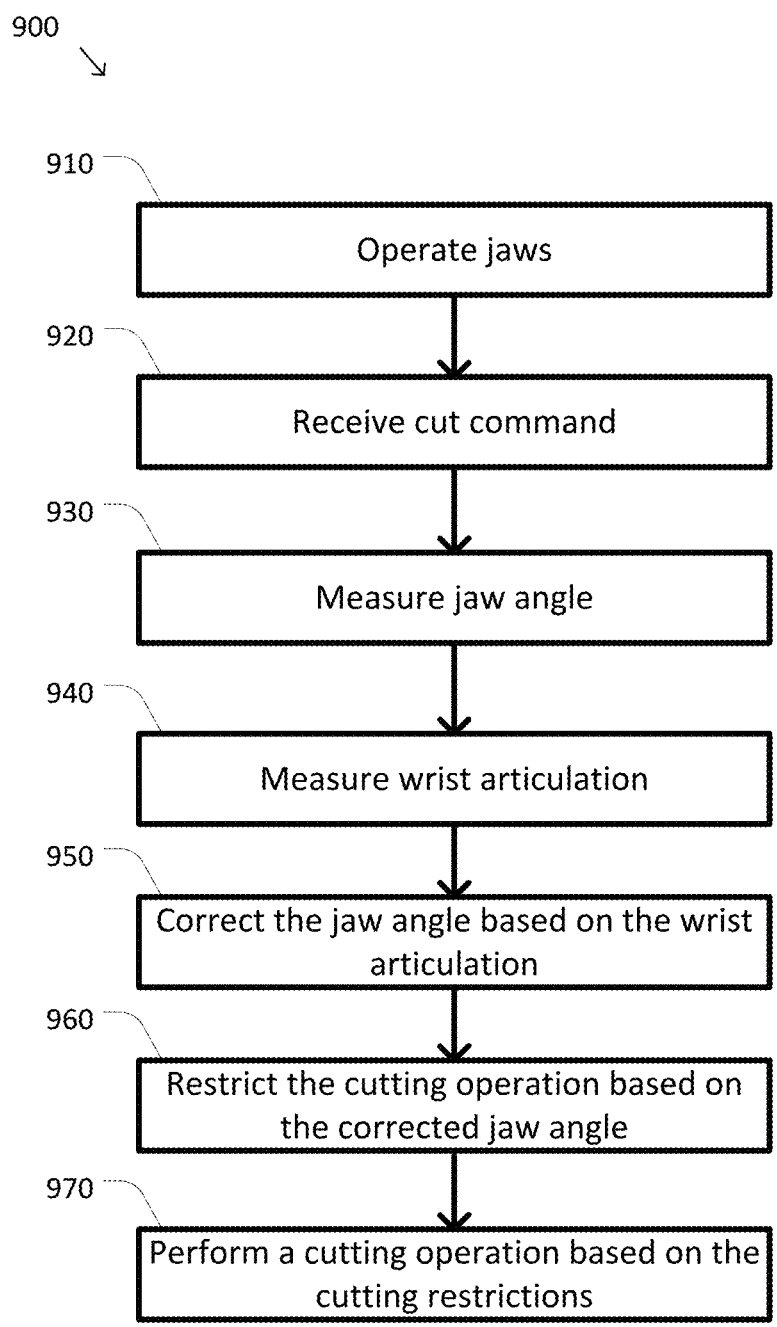
FIG. 9 is a simplified diagram of a method for performing a cutting operation according to some embodiments.

FIG. 9 is a simplified diagram of a method 900 for performing a cutting operation according to some embodiments. One or more of the processes 910-970 of method 900 may be implemented, at least in part, in the form of executable code stored on non-transient, tangible, machine readable media that when run by one or more processors (e.g., the processor 150 in control unit 140) may cause the one or more processors to perform one or more of the processes 910-970. In some embodiments, method 900 may be performed by an application, such as control application 170. In some embodiments, method 900 may be used to restrict and/or limit the movement of a cutting blade, such as cutting blade 330, based on an angle between gripper jaws, such as jaws 310, and flex in an articulated wrist, such as articulated wrist 230, of a surgical instrument, such as surgical instrument 200. In some embodiments, the cutting operation of method 900 may be performed according to models of FIGS. 7A, 7B, and 8. In some embodiments, drive components such as those described in FIGS. 2, 3, 4A-4C, 5, 6D and/or 6E may be used during the performance of method 900 to determine the angle between the gripper jaws so as to restrict and/or limit the movement of the cutting blade.

At a process 910, jaws of a surgical instrument are operated. In some examples, a surgeon and/or other medical personnel may use one or more controls of an operator console to position and/or operate the jaws, such as jaws 310, of the surgical instrument. In some examples, the surgeon and/or other medical personnel may manipulate one or more master controls, such as one or more master manipulators, levers, pedals, switches, keys, knobs, triggers, and/or the like to teleoperate the jaws to position them around appropriate tissue and/or other structures in preparation for a cutting operation. In some examples, the jaws may be operated to control their position and/or orientation as well as to adjust an angle between the jaws. In some examples, this operation may include adjusting a level of flex in an articulated wrist, such as articulated wrist 230, to orient the jaws as desired.

At a process 920, a cut command is received. In some examples, a surgeon and/or other personnel may request that a cutting operation take place. In some examples, the cutting operation may be requested using one or more master controls, such as one or more master manipulators, levers, pedals, switches, keys, knobs, triggers, and/or the like located on an operator console. In some examples, the requested cutting operation may be received by a control application, such as control application 170, via an interrupt, an input polling operation, an API call, and/or the like.

At a process 930, the jaw angle is measured. In some examples, the jaw angle may be measured using one of more position and/or rotation sensors. In some examples, the sensors may be located proximal to the jaws and may be configured to measure the jaw angle indirectly. In some examples, the sensors may be associated with one or more drive units, such as drive unit 500, that may be used to manipulate the DOF(s) of the jaws. In some examples, the sensors may measure a rotation angle of a capstan, such as capstan 510, and/or a rotation angle of a drive shaft, such as drive shaft 520. In some examples, when the jaws are controlled together, the jaw angle may be measured using the single drive unit for the jaws. In some examples, when the jaws are controlled independently, the jaw angle of each of the jaws may be measured separately and then combined to determine a composite measured jaw angle.

At a process 940, wrist articulation is measured. In some examples, the wrist articulation may be measured using one of more position and/or rotation sensors. In some examples, the sensors may be located proximal to the articulated wrist and may be configured to measure each of the articulation angles, such as pitch and/or yaw, of the articulated wrist indirectly. In some examples, the sensors may be associated with one or more drive units, such as drive unit 500, that may be used to manipulate the respective DOF for each of the joints of the articulated wrist. In some examples, the sensors may measure a rotation angle of a capstan, such as capstan 510, and/or a rotation angle of a drive shaft, such as drive shaft 520.

At a process 950, the jaw angle is corrected based on the wrist articulation. Using the jaw angle measured during process 930 and the wrist articulation measured during process 940, a corrected value for the jaw angle may be determined by the control application. In some examples, a jaw angle correction model, such as the jaw angle correction model of FIG. 8 and/or Equation 1 may be used to correct the jaw angle. In some examples, the jaw angle correction model may be determined based on a type of the surgical instrument and/or may be determined based on an identifier, such as a serial number, associated with the surgical instrument.

At a process 960, the cutting operation is restricted based on the corrected jaw angle. In some examples, the corrected jaw angle as determined during process 950 may be combined with a configurable tolerance for blade exposures to determine whether the cutting operation is to be restricted. Depending upon whether partial length cuts are permitted the cutting operation may be prevented from occurring and/or restricted to a maximum cutting length. In some examples, when partial length cuts are not permitted, the corrected jaw angle, the tolerance for blade exposures, and a desired cutting length are applied to a model, such as model 700 of FIG. 7A, to determine whether the corrected jaw angle is larger than a maximum permitted jaw angle. When the corrected jaw angle is larger than a maximum permitted jaw angle or jaw angle threshold the cutting operation is restricted to prevent it from occurring and/or a maximum permissible cutting length is set to zero. When the corrected jaw angle is equal to or smaller than the maximum permitted jaw angle, the cutting operation is not restricted and/or the maximum permissible cutting length is set to a full length cut. In some examples, when partial length cuts are permitted, the corrected jaw angle and the tolerance for blade exposures are applied to a model, such as model 750 of FIG. 7B, to determine the maximum permissible cutting length. The cutting operation is then restricted so that the cutting blade is not extended beyond the maximum permissible cutting length.

In some examples, when the cutting length is restricted, an audio, visual, and/or textual alert may be provided to the surgeon and/or other medical personnel to indicate that the cutting operation maximum permitted jaw angle has been exceeded when partial cuts are not allowed and/or when the cutting length is reduced to less than a full length cut.

At a process 970, a cutting operation is performed based on the cutting restrictions. In some examples, the cutting operation may be performed by extending the cutting blade and then retracing the cutting blade back into a garage. In some examples, the cutting operation may include driving the cutting blade according to a positional profile that may be adjusted to include a maximum extension based on the maximum cutting length, if any, determined during process 960. In some examples, the cutting blade may be extended and/or retracted based on force and/or torque applied to the cutting blade by a drive component, a drive mechanism, a drive unit, and/or an actuator such as a motor, solenoid, servo, active actuator, hydraulic actuator, pneumatic actuator, and/or the like. In some examples, when the maximum permissible cutting length is zero or the cutting operation is not permitted, process 970 may be skipped.

In some examples, the cutting operation may be monitored during process 970. In some examples, the actual position of the cutting blade and/or the drive unit for the cutting blade may be monitored using one or more sensors to determine whether the cutting blade and/or the drive unit are able to extend and/or retract the cutting blade as desired during the cutting operation. In some examples, when the cutting blade and/or the drive unit are not able to follow the extension and/or retraction within a predefined tolerance of a positional profile, an audio, visual, and/or textual alert may be provided to the surgeon and/or other medical personnel to indicate that the cutting operation may not have been successful. In some examples, the cutting operation may not be successful when the cutting blade is not able to extend to the maximum permissible cutting length. In some examples, the cutting operation may not be successful when the cutting blade becomes exposed and cannot return to the garage. In some examples, a warning and/or an alert using one or more audio, visual, and/or textual alerts may also be issued when any of the extracting and/or retracting operations reach a corresponding force and/or torque limit.

After the cutting operation is completed during process 970, another cut may be performed by returning to process 920 and/or the jaws may be repositioned before performing another cutting operation by returning to process 910.

Some examples of control units, such as control unit 140 may include non-transient, tangible, machine readable media that include executable code that when run by one or more processors (e.g., processor 150) may cause the one or more processors to perform the processes of method 900. Some common forms of machine readable media that may include the processes of method 900 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
   one or more processors; and
   a drive system comprising one or more drive units configured to be coupled to a cutting instrument,
   wherein the one or more processors are configured to:
      measure, using one or more first sensors, a jaw angle between gripping jaws of an end effector of the cutting instrument;
      measure, using one or more second sensors, articulation of an articulated wrist coupling the end effector to a shaft of the cutting instrument;
      correct the jaw angle based on the articulation of the articulated wrist;
      determine a cutting length based on the corrected jaw angle; and
      perform, using the drive system, a cutting operation according to the cutting length.

2. The computer-assisted device of claim 1, wherein the cutting operation comprises an extension and a retraction of a cutting blade.

3. The computer-assisted device of claim 1, wherein the jaw angle is measured at the drive system.

4. The computer-assisted device of claim 1, wherein the articulation of the articulated wrist is measured at the drive system.

5. The computer-assisted device of claim 1, wherein the cutting length is less than a full-length cutting length.

6. The computer-assisted device of claim 1, wherein to correct the jaw angle, the one or more processors are configured to adjust the measured jaw angle based on a correction model.

7. The computer-assisted device of claim 6, wherein the correction model is linear.

8. The computer-assisted device of claim 1, wherein the articulation of the articulated wrist comprises one or more of a pitch angle or a yaw angle.

9. The computer-assisted device of claim 8, wherein to correct the jaw angle, the one or more processors are configured to adjust the measured jaw angle proportional to one or more of an absolute value of the pitch angle or an absolute value of the yaw angle.

10. The computer-assisted device of claim 1, wherein the one or more processors are further configured to:
    determine a restriction on the cutting operation based on the corrected jaw angle; and
    perform or prevent the cutting operation according to the restriction.

11. The computer-assisted device of claim 10, wherein the restriction on the cutting operation is to prevent the cutting operation when the corrected jaw angle is greater than a jaw angle threshold.

12. A method comprising:
    measuring, by one or more processors and using one or more first sensors, a jaw angle between gripping jaws of an end effector of a cutting instrument;
    measuring, by the one or more processors and using one or more second sensors, articulation of an articulated wrist coupling the end effector to a shaft of the cutting instrument;
    correcting, by the one or more processors, the jaw angle based on the articulation of the articulated wrist;
    determining, by the one or more processors, a cutting length based on the corrected jaw angle; and
    performing, using a drive system comprising one or more drive units coupled to the cutting instrument, a cutting operation according to the cutting length.

13. The method of claim 12, wherein the cutting length is less than a full-length cutting length.

14. The method of claim 12, wherein:
    the articulation of the articulated wrist comprises one or more of a pitch angle or a yaw angle; and
    correcting the jaw angle comprises adjusting the measured jaw angle proportional to one or more of an absolute value of the pitch angle or an absolute value of the yaw angle.

15. The method of claim 12, further comprising measuring the jaw angle at the drive system.

16. The method of claim 12, further comprising measuring the articulation of the articulated wrist at the drive system.

17. A non-transitory machine-readable medium comprising a plurality of machine-readable instructions which when executed by one or more processors associated with a computer-assisted device are adapted to cause the one or more processors to perform a method comprising:
    measuring, using one or more first sensors, a jaw angle between gripping jaws of an end effector of a cutting instrument;
    measuring, using one or more second sensors, articulation of an articulated wrist coupling the end effector to a shaft of the cutting instrument;
    correcting the jaw angle based on the articulation of the articulated wrist;
    determining a cutting length based on the corrected jaw angle; and
    performing, using a drive system comprising one or more drive units coupled to the cutting instrument, a cutting operation according to the cutting length.

18. The non-transitory machine-readable medium of claim 17, wherein the cutting length is less than a full-length cutting length.

19. The non-transitory machine-readable medium of claim 17, wherein:

the articulation of the articulated wrist comprises one or more of a pitch angle or a yaw angle; and correcting the jaw angle comprises adjusting the measured jaw angle proportional to one or more of an absolute value of the pitch angle or an absolute value of the yaw angle.

20. The non-transitory machine-readable medium of claim 17, further comprising:

measuring the jaw angle at the drive system; and measuring the articulation of the articulated wrist at the drive system.

* * * * *

UNITED STATES PATENT AND TRADEMARK OFFICE
CERTIFICATE OF CORRECTION

PATENT NO. : 11,712,300 B2
APPLICATION NO. : 16/930239
DATED : August 1, 2023
INVENTOR(S) : David W. Weir et al.

Page 1 of 1

It is certified that error appears in the above-identified patent and that said Letters Patent is hereby corrected as shown below:

On the Title Page

(63) Related U.S. Application Data:
Please delete "Continuation of application No. 15/573,031, filed as application No. PCT/US2016/032324 on May 13, 2016, now Pat. No. 10,743,897." and insert --Continuation of application No. 15/573,031, filed on Nov. 9, 2017, now Pat. No. 10,743,897, which is a 371 of application No. PCT/US2016/032324, filed on May 13, 2016.--.

Signed and Sealed this
Fifth Day of September, 2023

Katherine Kelly Vidal
*Director of the United States Patent and Trademark Office*